(12) United States Patent
Grass et al.

(10) Patent No.: US 11,071,504 B2
(45) Date of Patent: Jul. 27, 2021

(54) CALIBRATION-FREE TOMOSYNTHESIS

(71) Applicant: KONINKLIJKE PHILIPS N.V., Eindhoven (NL)

(72) Inventors: Michael Grass, Buchholz in der Nordheide (DE); Dirk Schaefer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 245 days.

(21) Appl. No.: 16/305,246

(22) PCT Filed: Jun. 5, 2017

(86) PCT No.: PCT/EP2017/063596
§ 371 (c)(1),
(2) Date: Nov. 28, 2018

(87) PCT Pub. No.: WO2017/211755
PCT Pub. Date: Dec. 14, 2017

(65) Prior Publication Data
US 2020/0315551 A1    Oct. 8, 2020

(30) Foreign Application Priority Data
Jun. 7, 2016  (EP) .................................... 16173239

(51) Int. Cl.
*A61B 6/02*  (2006.01)
*A61B 6/00*  (2006.01)

(52) U.S. Cl.
CPC ............ *A61B 6/025* (2013.01); *A61B 6/4007* (2013.01); *A61B 6/4452* (2013.01); *A61B 6/466* (2013.01); *A61B 6/5205* (2013.01)

(58) Field of Classification Search
None
See application file for complete search history.

(56) References Cited

U.S. PATENT DOCUMENTS 8,094,773 B2    1/2012 Boese et al.
2007/0122020 A1    5/2007 Claus
(Continued)

FOREIGN PATENT DOCUMENTS

JP    20160366771 A    3/2016
WO    2008018510 A1    2/2008
WO    2015058980 A1    4/2015

OTHER PUBLICATIONS

Tomkowiak, Michael T. et al "Calibration-Free Device sizing using an Inverse Geometry X-Ray System", Am. Assoc. Medical Physics, vol. 38, No. 1, Jan. 2011.
(Continued)

*Primary Examiner* — Edwin C Gunberg

(57) ABSTRACT

The present invention relates to tomosynthesis. In order to further facilitate and improve the generation of three-dimensional image data, an X-ray imaging system (10) for calibration-free tomosynthesis is provided. The system comprises an imaging arrangement (12) with an X-ray detector unit (14) and an X-ray unit (16) comprising a plurality of X-ray sources (18). The system also comprises an image processing unit (20), an object receiving space (22), and a moving unit (24) for providing a relative movement between the imaging arrangement and an object of interest arranged at least partially in the object receiving space. The X-ray sources are provided in a known spatial relationship; the X-ray detector unit and the X-ray unit are also provided in a known spatial detector-sources-relationship. The moving unit provides a relative movement between the object of interest and the imaging arrangement in order to provide a plurality of system-to-object positions. The X-ray unit is configured to provide X-ray radiation to the object of interest from a plurality of different directions for each system-to-object position in order to provide a plurality of subsets of views with different viewing directions. The (Continued)

processing unit is configured to determine positions of the object in relation to the imaging arrangement based on the subsets of views, and to calculate a three-dimensional geometric position for each view of the subsets of views, and also to calculate a three-dimensional tomosynthesis reconstruction volume from the plurality of subsets of views.

12 Claims, 3 Drawing Sheets

(56) References Cited

U.S. PATENT DOCUMENTS

| | | | |
|---|---|---|---|
| 2008/0186311 A1* | 8/2008 | Claus | A61B 6/583 345/420 |
| 2012/0014501 A1* | 1/2012 | Pelc | G06T 7/0012 378/9 |
| 2014/0119500 A1 | 5/2014 | Akahori | |
| 2015/0016586 A1 | 1/2015 | Maurer | |
| 2015/0030119 A1 | 1/2015 | Tamura et al. | |
| 2015/0359504 A1 | 12/2015 | Zhou | |

OTHER PUBLICATIONS

Speidel, Michael et al "Feasibility of Low-Dose single-View 3D Fiducial Tracking Concurrent with External Beam Delivery", Am. Assoc. Medical Physics, vol. 39, No. 4, Apr. 2012.

Speidel, Michael et al, 'Three-Dimensional Tracking of Cardiac Catheters using an Inverse Geometry X0Ray Fluoroscopy System', Am. Assoc. Medical Physics, vol. 37, No. 12, Dec. 2010.

* cited by examiner

CALIBRATION-FREE TOMOSYNTHESIS

CROSS-REFERENCE TO PRIOR APPLICATIONS

This application is the U.S. National Phase application under 35 U.S.C. § 371 of International Application No. PCT/EP2017/063596, filed on Jun. 5, 2017, which claims the benefit of European Patent Application No. 16173239.1, filed on Jun. 7, 2016. These applications are hereby incorporated by reference herein.

FIELD OF THE INVENTION

The present invention relates to tomosynthesis, and relates in particular to an X-ray imaging system for calibration-free tomosynthesis and to a method for tomosynthesis reconstruction, as well as to a computer program element and a computer-readable medium.

BACKGROUND OF THE INVENTION

Tomosynthesis is used, for example, in medical imaging. In tomosynthesis, the cone angle of an X-ray beam may be used to calculate quasi-three-dimensional information from a plurality of two-dimensional projections. For example, an X-ray source and a detector are provided in combination with a planar relative system-to-object motion, but an accurate system calibration is necessary for the tomosynthesis reconstruction. It has been shown that calibration can be burdensome. US 2008/0186311 A1 describes a method and system for three-dimensional imaging in a non-calibrated geometry.

SUMMARY OF THE INVENTION

However, there may still be a need to further facilitate and improve the generation of three-dimensional image data.

The object of the present invention is solved by the subject-matter of the independent claims; further embodiments are incorporated in the dependent claims. It should be noted that the following described aspects of the invention apply also for the X-ray imaging system for calibration-free tomosynthesis, for the method for tomosynthesis reconstruction and for the computer program element as well as for the computer-readable medium.

According to the present invention, an X-ray imaging system for calibration-free tomosynthesis is provided. The system comprises an imaging arrangement with an X-ray detector unit and an X-ray unit comprising a plurality of X-ray sources. The system further comprises an image processing unit, an object receiving space and a moving unit for providing a relative movement between the imaging arrangement and an object of interest arranged at least partially in the object receiving space. The X-ray sources are provided in a known spatial relationship; the X-ray detector unit and the X-ray unit are also provided in a known spatial detector-sources-relationship. The moving unit provides a relative movement between the imaging arrangement and the object of interest in order to provide a plurality of system-to-object positions. The X-ray unit is configured to provide X-ray radiation to the object of interest from a plurality of different directions for each system-to-object position in order to provide a plurality of subsets of views with different viewing directions. The processing unit is configured to determine a three-dimensional geometric position for each of the subsets of views, and also to calculate a three-dimensional tomosynthesis reconstruction volume from the plurality of subsets of views using the determined geometric positions of each subset.

According to the present invention, also a method for tomosynthesis reconstruction is provided. The method comprising the following steps:
a) Generating a plurality of subsets of views by providing X-ray radiation to an object of interest from a plurality of different directions with a plurality of X-ray sources and detecting the X-ray radiation with a detector. The plurality of X-ray sources and the detector are forming an imaging arrangement and are provided in a known spatial relationship. For the plurality of subsets of views, the imaging arrangement and the object are arranged in a plurality of spatial arrangement-object positions.
b) Determining a three-dimensional geometric position for each of the subsets of views.
c) Calculating a three-dimensional tomosynthesis reconstruction volume from the plurality of subsets of views using the determined geometric positions of each subset.

The arrangement and use of an X-ray unit with a plurality of X-ray sources already provides three-dimensional information, which is used in a calculation of three-dimensional geometric positions for each of the subsets of views and thus for each of the system-object positions. In this respect, a "geometric positions" of a subset of views is a 3D position of such subset within a common coordinate system.

Thus, three-dimensional geometric position data in relation to a subsequent or preceding subset of views is provided based on one or more views or images in each subset, for example determined in relation to visible structures on the X-ray projections. Thus, the three-dimensional situation can be calculated and hence a so-to-speak calibration alternative is provided.

According to an example, X-ray radiation is provided simultaneously to different portions of the detector.

This results in the acquisition of multiple X-ray views and respective image data at the same point in time.

According to an example, additionally or alternatively, X-ray radiation is provided successively to the same portion of the detector.

The stepwise provision of X-ray radiation from the plurality of X-ray sources for the same spatial arrangement allows to make use of a larger detector surface. In this case, however, image acquisition speed is determined by the readout time of the individual detector portions.

According to an example, the radiation is provided to a plurality of detectors.

According to an example, the moving unit is configured to provide a linear relative movement between the object and the imaging arrangement. For example, the imaging arrangement is moved along a linear path with respect to the object, the linear path being aligned with an anatomical structure of interest, such as a human leg during a peripheral angiography procedure.

For instance, a patient table or support on which the object resides, may be configured to carry out a linear movement with respect to the imaging arrangement. Alternatively or in addition, the imaging arrangement itself moves along an elongated object.

In this example, the three-dimensional tomosynthesis reconstruction volume results in a so-called "long view" tomosynthesis image of an elongated object.

Alternatively, based on the examination to be performed, different shaped movement paths, such as circular paths or paths that are curved in accordance with an anatomy of interest, may be considered.

According to an example, relating to the method described above, the determining in step b) is based on three-dimensional positions of landmarks in the views. Landmarks may be identified in one or more views of different subsets, and a registration of different subsets may then be carried out based on landmarks that have been identified in each of these subsets. For example, when the fields of view in adjacent system-object positions have sufficient overlap, landmarks identifiable in one subset of views may typically also be identifiable in the subsequent or preceding subset.

According to another example, the determining in step b) is based on local three-dimensional volumes that are registered to each other based on a three-dimensional registration, in particular a 3D-3D registration. For example, the local 3D volumes are reconstructed from individual subsets of views.

In both options, which may also be combined, the determination of the geometric position is based on image content, namely the landmarks or on the information retrieved from registering consecutive image data sets.

According to an example, each subset of a plurality of subsequent subsets is registered to the respective previous subset in order to provide interrelated three-dimensional image data for the tomosynthesis reconstruction.

According to an aspect, the geometric calibration of the system-to-object position is based on landmarks or on local three-dimensional reconstructions. The landmarks may be anatomical landmarks (bone structures) or a part of the table while the local three-dimensional reconstructions are generated from a subset of views. A geometric position is determined from the subsets of views which are acquired parallel in time and a geometry is used in the subsequent tomosynthesis reconstruction.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
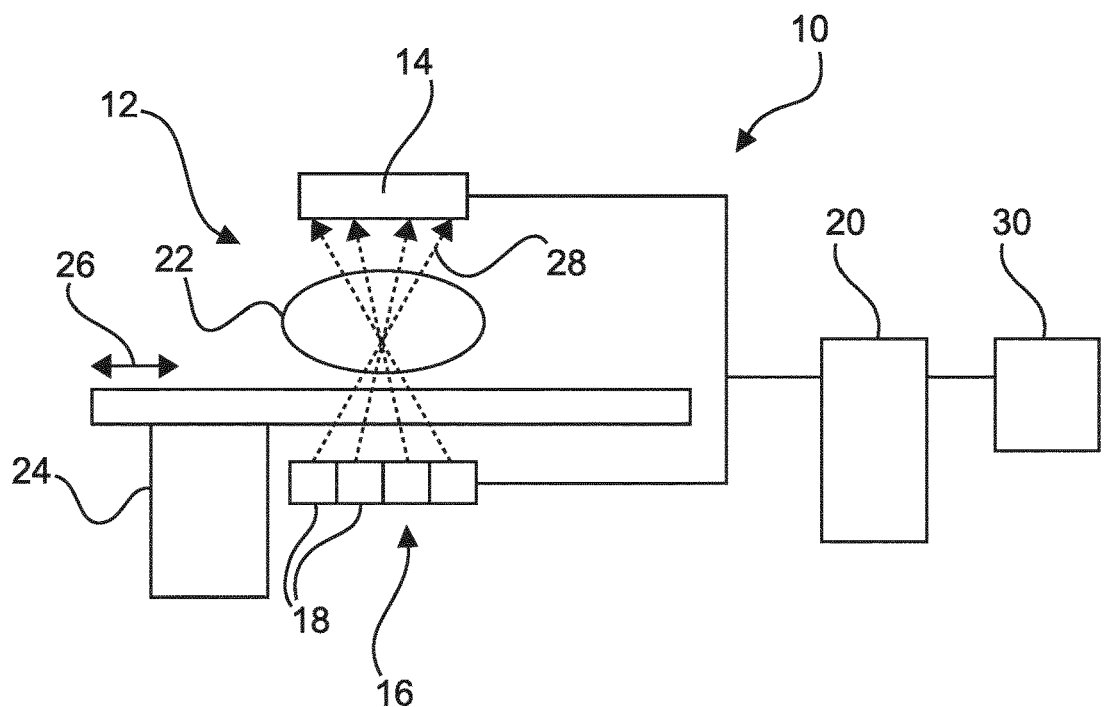
FIG. 1 shows a schematic setup of an example of an X-ray imaging system for calibration-free tomosynthesis.

FIG. 1 shows an X-ray imaging system 10 for calibration-free tomosynthesis. The system comprises an imaging arrangement 12 with an X-ray detector unit 14 and an X-ray unit 16 comprising a plurality of X-ray sources 18. Further, an image processing unit 20 is provided. Still further, an object receiving space 22, indicated by an oval line, is provided. Still further, a moving unit 24 is arranged for providing a relative movement between the imaging arrangement and an object of interest arranged at least partially in the object receiving space. The relative movement is indicated by a double arrow 26. For example, the moving unit comprises a support table or a support surface for receiving the object of interest. The support surface or patient table may be movable in relation to the imaging arrangement 12. In another example, the object receiving arrangement is fixed and the imaging arrangement 12 is provided to be movable. In a still further example, both imaging arrangement 12 and object receiving or support surface are mutually movable in relation to each other.

The X-ray sources are provided in a known spatial relationship and the X-ray detector unit 14 and the X-ray unit 16 are also provided in a known spatial detector-sources-relationship. The moving unit 24 provides a relative movement between the object of interest and the imaging arrangement 12 in order to provide a plurality of system-to-object positions for example positioned along the movement direction 26.

The X-ray unit 16 is configured to provide X-ray radiation of the object of interest from a plurality of different directions for each system-to-object position in order to provide a plurality of subsets of views with different viewing directions. In FIG. 1, the individual views and their different viewing directions are indicated with hashed arrow lines 28. The processing unit 20 is configured to determine positions of the object in relation to the imaging arrangement 12 based on the subsets of views and to calculate a three-dimensional geometric position for each view of the subsets of views and to calculate a three-dimensional tomosynthesis reconstruction volume from the plurality of subsets of views.

As an option, a display unit 30 may be provided in order to display the reconstructed image volume information.

In an example, the X-ray unit is configured to provide radiation to an object of interest from a plurality of different directions in a single spatial detector-source-relationship position in order to provide X-ray image data relating to different viewing directions 28.

The plurality of X-ray sources is also referred to as multi-source. The system is provided as a multi-source X-ray system.

In an example, the tomosynthesis relates to long-view tomosynthesis, wherein an elongated volume is reconstructed using a tomosynthesis algorithm. The elongated volume may for example correspond to an extremity of a human body, such as a leg.

Figure 2:
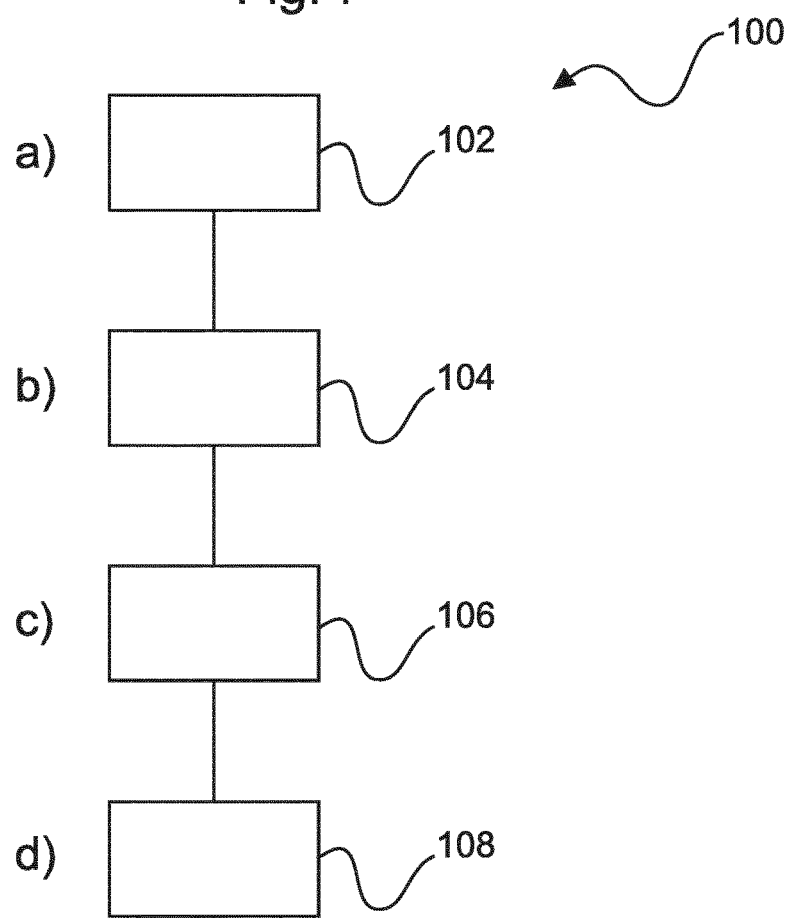
FIG. 2 shows an example of a method for tomosynthesis reconstruction.

FIG. 2 shows a method 100 for tomosynthesis reconstruction. The method comprises the following steps:

In a first step 102, also referred to as step a), a plurality of subsets of views is generated by providing X-ray radiation to an object of interest from a plurality of different directions with a plurality of X-ray sources and the X-ray radiation is detected with a detector. The plurality of X-ray sources and the detector are forming an imaging arrangement and are provided in a known spatial relationship. For the plurality of subsets of views, the imaging arrangement and the object are arranged in a plurality of spatial arrangement-object positions.

In an optional second step 104, positions of the object in relation to the imaging arrangement are determined based on the subsets of views.

In a third step 106, also referred to as step b), a three-dimensional geometric position is determined for each of the subsets of views.

In a fourth step 108, also referred to as step c), a three-dimensional tomosynthesis reconstruction volume is calculated from the plurality of subsets of views using the determined geometric reconstructions for each subset.

For a subset of views, the X-ray radiation is provided to the object from a plurality of different directions with a plurality of X-ray sources. For example, for a first subset of views, the imaging arrangement and the object are arranged in a first spatial position, and for a further, e.g. second, subset of views, the imaging arrangement and the object are arranged in a further, e.g. second spatial position. The object may for example be an extremity of the human body such as a leg, and the different spatial system-object positions may for example be provided along a linear path aligned with the anatomy of interest.

In an example, in step a), the provided X-ray radiation forms a plurality of X-ray projections.

In a further example, the determining in step b) is based on three-dimensional positions of landmarks in the images.

The term "landmark" relates to visible structures, such as a structure with high contrast, which can be detected in a projection, for example bones in tissue, tissue-to-air boundaries, or bones-to-tissue boundaries. Further, also implants, prosthesis, catheters and the like can be used as landmarks, as long as they remain their spatial position during acquisition. Further, also extremal points of the structures can be used as landmarks for the determination.

In a further example, not further shown, the determining in step b) is based on local 3D dimensional volumes that are registered to each other based on a three-dimensional registration. Each local 3D volumes may for example be reconstructed from a single subset of views, thus each local 3D volume may correspond to a system-object position.

In an example the three-dimensional registration is provided as a 3D-3D registration.

In an example, the tomosynthesis reconstruction is provided as calibration-free process.

In a further example, each subset of a plurality of subsequent subsets is registered to the respective previous subset in order to provide interrelated three-dimensional image data for the tomosynthesis reconstruction, such as a long-view tomosynthesis reconstruction of, for example, an extremity of a patient during a peripheral angiography procedure.

In a further example, for each subset, a plurality of X-ray projections i.e. at least a part of the views within the subset are provided parallel in time. Preferably, for projections acquired parallel in time, the X-ray radiation is detected by a plurality of different detector areas. In other words, the object is projected onto multiple different areas of the detector simultaneously.

In a further example, for each subset, a plurality of X-ray projections i.e. at least a part of the views within the subset are provided as successive projections and successive readouts of the detector are provided accordingly. In this case, for example, the entire detector surface may be used as a single portion or area for each successive view In an example, a very fast sequence of successive projections is provided. For example, the sequence is determined by the fastest possible readout time.

In a further example, simultaneous and successive detections as described above are combined.

Figure 3:
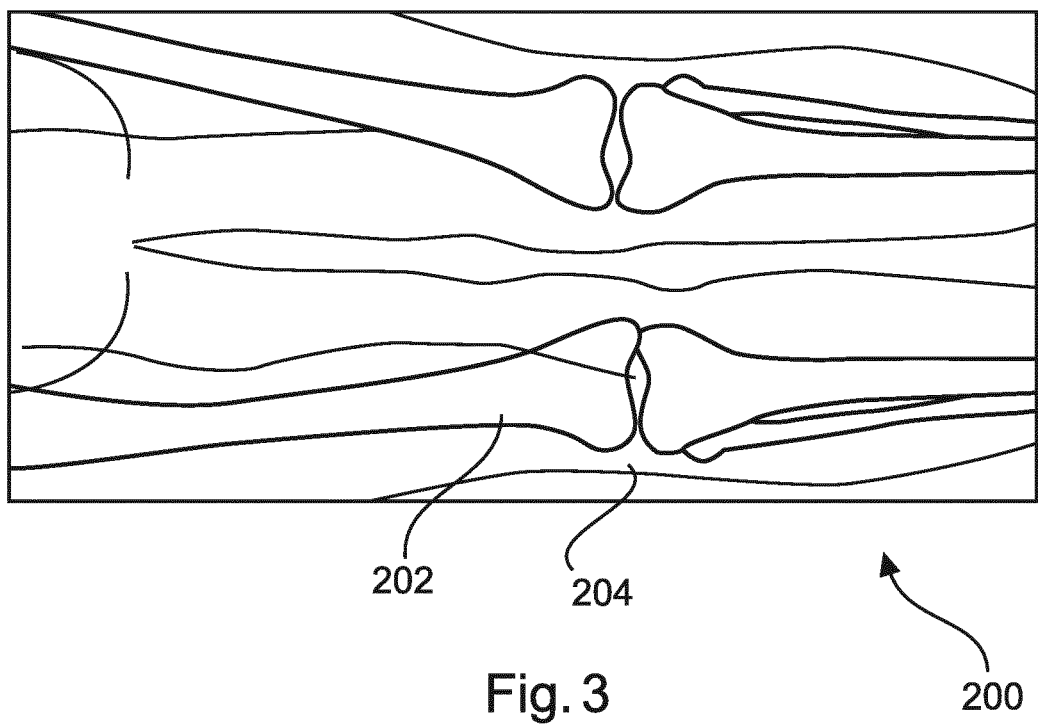
FIG. 3 shows an example of three-dimensional X-ray image data achieved.

In FIG. 3, an image 200 is shown, which image is generated from tomosynthesis image data. The image shows, as an example, a lower limb structure of a patient, for example showing two legs, for which a respective bone structure 202 and a surrounding tissue structure 204 is visible.

In order to achieve the respective necessary X-ray projection data for the tomosynthesis reconstruction, an X-ray multi-block with a plurality of X-ray sources may be provided.

Figure 4:
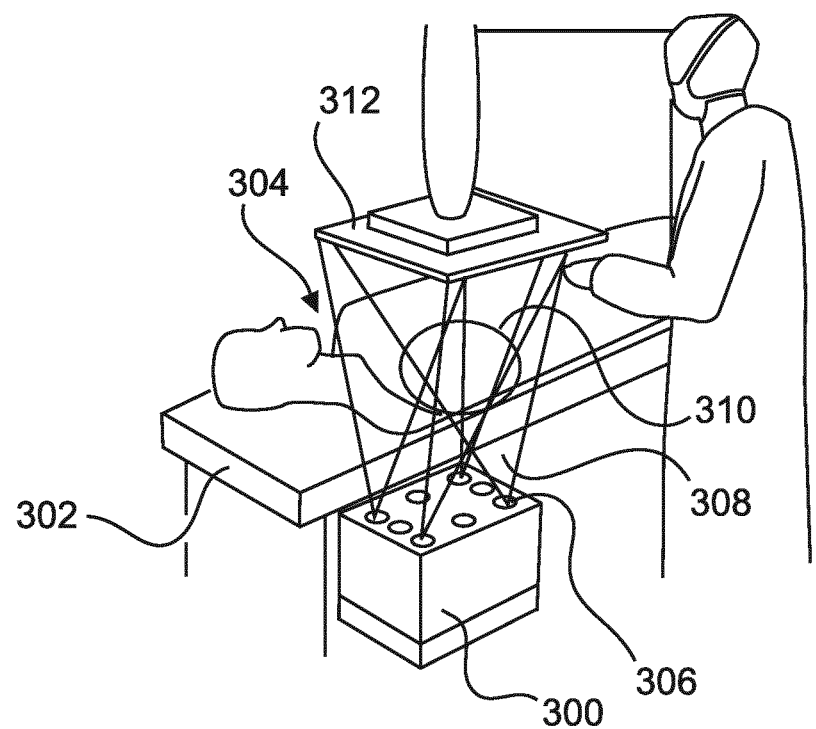
FIG. 4 shows a further exemplary setup of an X-ray imaging system.

For example, FIG. 4 shows a first arrangement, having an X-ray multi-block 300 below a patient table 302. Above the patient table 302, as an example, a patient 304 is provided as an object of interest. The X-ray multi-block 300 comprises a plurality of X-ray sources 306 that generate a plurality of X-ray beams 308. The X-ray beams radiate the object of interest in a region of interest, indicated with a circular line 310. Hence, the plurality of X-ray beams 308 passes that region of interest 310 and then reaches a detector 312 for readout purposes. For example, the X-ray beams hit the X-ray detector 312 at different areas, thus providing different image information for the different sets of views.

For example, the example shown in FIG. 4 may comprise the projection acquisition parallel in time, i.e. the X-ray beams hit the X-ray detector at the same time and the respective portions are then read out.

Figure 5:
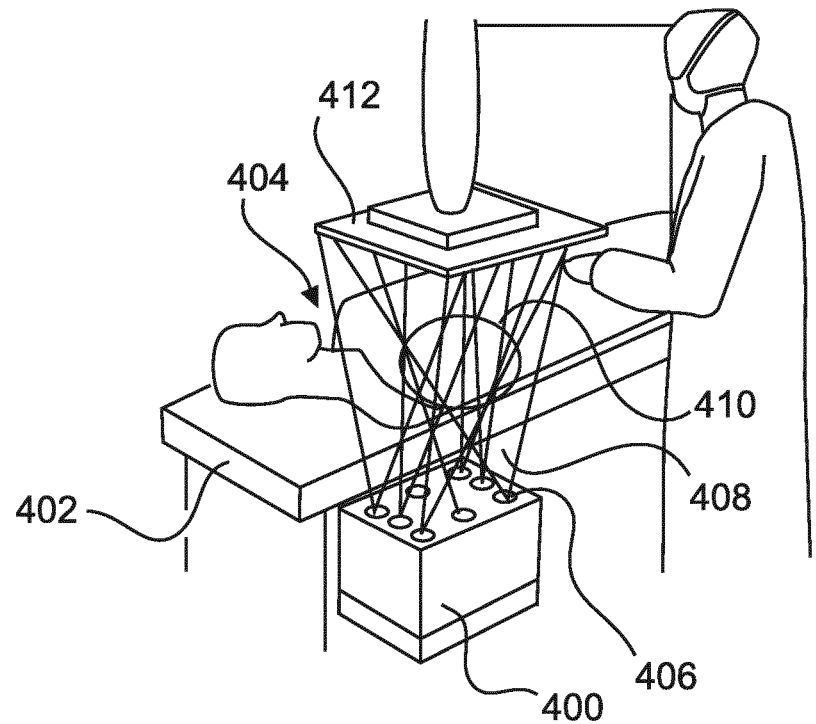
FIG. 5 shows a further example of a setup of an X-ray imaging system.

FIG. 5 shows a further example, where an X-ray multi-block 400 is provided below a patient table or patient support 402. An object of interest 404 is provided in a similar manner. The X-ray multi-block 400 comprises a plurality of X-ray sources 406 and generates a respective plurality of X-ray beams 408 passing a region of interest 410 of the object. A detector 412 is provided to detect the X-ray radiation and provide the data for further processing as described above.

In a further example, for example shown in FIG. 5, the plurality of X-ray beams is provided in a successive manner, however being as fast as possible.

For both examples, X-ray image information relating to different viewing directions are provided for the same, or nearly the same, point in time. Hence, as a registration, landmark positions in 3D may be used or a registration of successive 3D projections in order to perform a 3D-3D registration.

In an example, at least three X-ray sources are provided, for example three to five X-ray sources, or more than five X-ray sources.

In addition to the shown examples, it may also be provided that the radiation is provided successively to the same detector portions, or to different detector portions simultaneously. In an example, not further shown, the radiation is provided to a plurality of detectors.

As already indicated above, the moving unit, for example supporting in the patient table, is configured to provide a linear relative movement between an object and the imaging arrangement.

In a further example, a movement between an object and the imaging arrangement is provided along a moving path that is aligned with an anatomical structure, such as e.g. the aorta or the legs' bones structure.

In a further example, a movement between an object and the imaging arrangement is provided as a circular movement with a floating table In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging system for calibration-free tomosynthesis, the system comprising:
   an X-ray detector and a plurality of X-ray sources;
   an image processor;
   an object receiving space; and
   a moving surface configured to provide a relative movement between the X-ray detector and the plurality of X-ray sources relative to an object of interest arranged at least partially in the object receiving space interest in order to provide a plurality of system-to-object positions;
   wherein the plurality of X-ray sources are provided in a known spatial relationship; and wherein the X-ray detector the plurality of X-ray sources are provided in a known spatial detector-sources relationship;
   wherein the plurality of X-ray sources are configured to provide X-ray radiation to the object of interest from a plurality of different directions for each system-to-object position in order to provide a plurality of subsets of views with different viewing directions; and
   wherein the image processor is configured to determine a three-dimensional geometric position for each of the subsets of views based on three-dimensional positions of landmarks or local three-dimensional reconstructions in one or more views of different subsets; and
   to calculate a three-dimensional tomosynthesis reconstruction volume from the plurality of subsets of views using the determined geometric positions of each subset.

2. The system according to claim 1, wherein X-ray radiation is provided simultaneously to different portions of the X-ray detector.

3. The system according to claim 1, wherein X-ray radiation is provided successively to a same portion of the X-ray detector.

4. The system according to claim 1, wherein the radiation is provided to a plurality of X-ray detectors.

5. The system according to claim 1, wherein the moving surface is configured to provide a linear relative movement between an object relative to the plurality of X-ray sources and X-ray detector.

6. The system according to claim 5, wherein a patient table or support on which the object resides is configured to carry out a linear movement with respect to the plurality of X-ray sources and X-ray detector.

7. A method for tomosynthesis reconstruction, the method comprising the following steps:
   generating a plurality of subsets of views by providing X-ray radiation to an object of interest from a plurality of different directions with a plurality of X-ray sources and detecting the X-ray radiation with a detector;
   wherein the plurality of X-ray sources and the detector are provided in a known spatial relationship; and
   wherein, for the plurality of subsets of views, the plurality of X-ray sources, the detector, and the object are arranged in a plurality of spatial arrangement-object positions;
   determining a three-dimensional geometric position for each of the subsets of views based on three-dimensional positions of landmarks or local three-dimensional reconstructions in one or more views of different subsets; and
   calculating a three-dimensional tomosynthesis reconstruction volume from the plurality of subsets of views using the determined geometric positions of each subset.

8. The method according to claim 7, wherein determining a three-dimensional position is based on local three-dimensional volumes corresponding to individual subsets, which are registered to each other based on a three-dimensional registration.

9. The method according to claim 8, wherein each subset of a plurality of subsequent subsets is registered to the respective previous subset in order to provide interrelated three-dimensional image data for the tomosynthesis reconstruction.

10. The method according to claim 7, wherein for each subset, the plurality of X-ray projections is provided parallel in time, whereby X-ray radiation for said projections is detected by a plurality of different detector areas.

11. The method according to claim 7, wherein for each subset, the plurality of X-ray projections is provided as successive projections and successive read-outs of the detector are provided accordingly.

12. A non-transitory computer readable medium having stored thereon a computer program including instructions that, when executed by a processor, is configured to perform the method steps of claim 7.

* * * * *